United States Patent [19]

Lyshkow

[11] 4,032,297

[45] June 28, 1977

[54] POLLUTION MONITORING APPARATUS

[75] Inventor: Norman A. Lyshkow, Chicago, Ill.

[73] Assignee: Combustion Equipment Associates, Inc., Stanford, Conn.

[22] Filed: Sept. 29, 1975

[21] Appl. No.: 617,855

Related U.S. Application Data

[63] Continuation of Ser. No. 479,227, June 14, 1974, abandoned.

[52] U.S. Cl. .......................... 23/254 E; 23/232 E; 23/255 E

[51] Int. Cl.² ................. G01N 21/14; G01N 21/48; G01N 21/30

[58] Field of Search ......... 23/232 R, 254 R, 232 E, 23/254 E, 253 TP, 230 PC, 253 PC, 255 E

[56] References Cited

UNITED STATES PATENTS

| | | | |
|---|---|---|---|
| 2,800,397 | 7/1957 | Offutt et al. | 23/232 R |
| 2,895,807 | 7/1959 | Sorg et al. | 23/232 R X |
| 3,111,391 | 11/1963 | Filippi | 23/254 E |
| 3,460,153 | 8/1969 | White | 23/254 R |
| 3,705,014 | 12/1972 | Townsley | 23/230 PC |

Primary Examiner—R.E. Serwin

[57] ABSTRACT

Apparatus for the detection and/or analysis of pollutant gases comprising a light-reflective surface sensitive to a pollutant gas which is capable of reaction with the pollutant gas to cause a decrease in the reflectivity of the surface, light source means positioned to pass a beam of light angularly onto the surface and light-sensing means positioned to receive light reflected from the surface and means to contact a gas stream containing the pollutant gas with the surface whereby the decrease in light-reflectivity serves as a measure of the concentration of the pollutant gas in the sample and the rate of decrease in reflectivity serves as a measure of the dose rate of the pollutant gas to which one in the environment from which the pollutant gas is taken is subjected.

13 Claims, 10 Drawing Figures

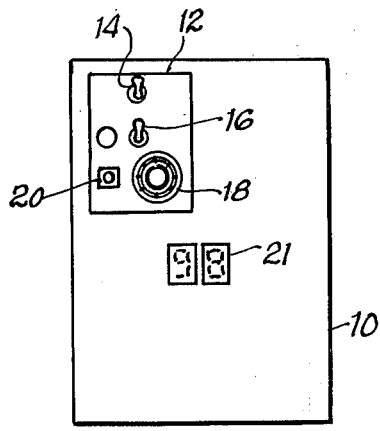
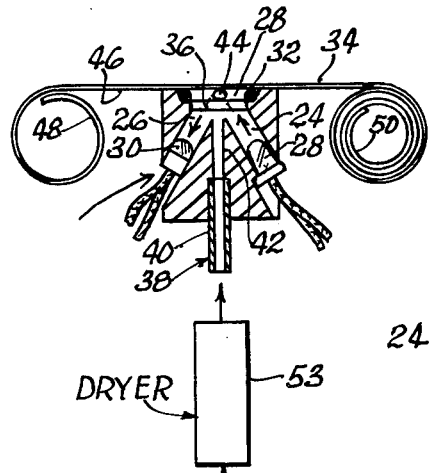
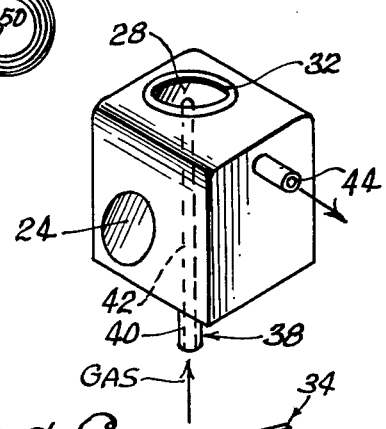
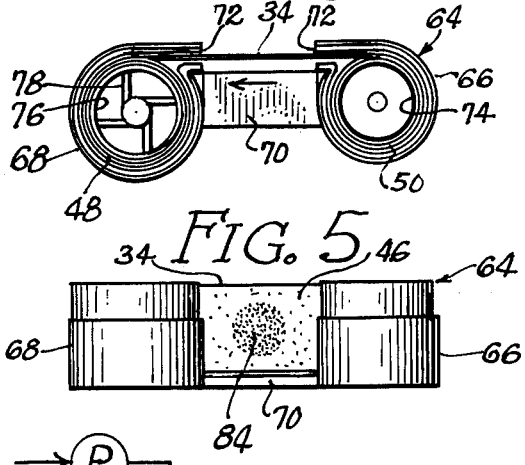
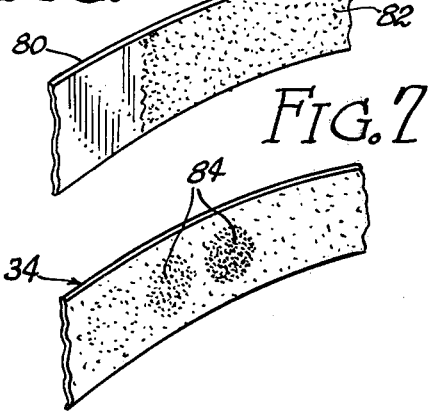
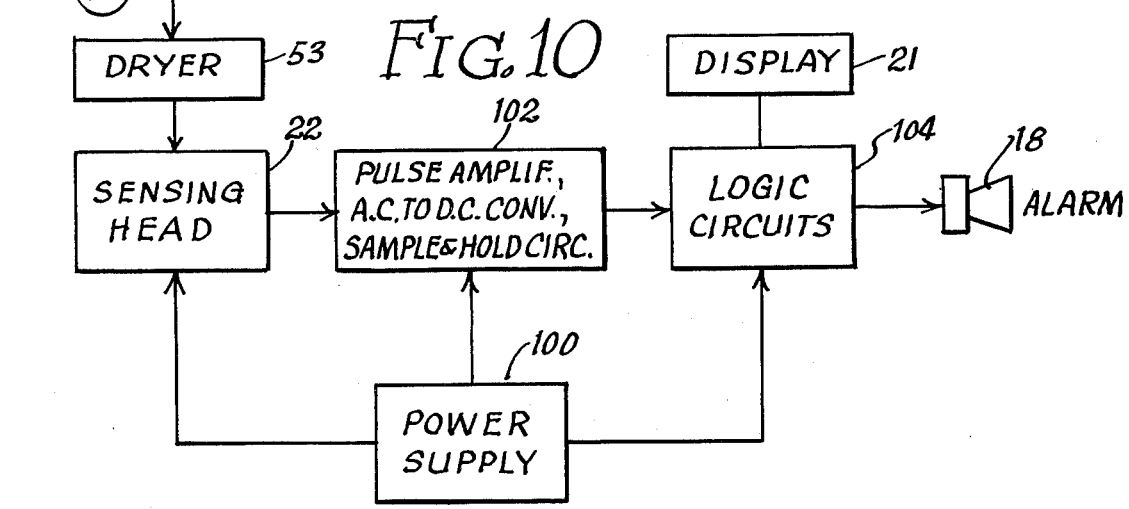

POLLUTION MONITORING APPARATUS

This is a continuation of application Ser. No. 479,227 filed June 14, 1974, and now abandoned.

This invention relates to apparatus for detecting and/or measuring pollutant gases, and more particularly to apparatus capable of monitoring pollutant gases.

A variety of pollution monitoring equipment is currently available, and includes colormetric equipment in which an ambient atmosphere is passed through the apparatus whereby pollutant gases react with a color-forming liquid to develop color, the intensity of which is proportional to the concentration of pollutant gases in atmosphere. However, such colormetric equipment is frequently bulky and cannot be carried about by an individual to continuously or intermittently monitor the dose and/or the dose rate of pollutant gases to which an individual is subjected.

It is accordingly an object of the present invention to provide apparatus for monitoring pollutant gases which overcomes the foregoing deficiencies, and it is a more specific object of the invention to provide apparatus for monitoring pollutant gases which is small in physical size and can be conveniently transported by an individual in an atmosphere containing one or more pollutant gases to measure the dose and/or the dose rate of such gases to which an individual is subjected.

It is another object of the present invention to provide apparatus for monitoring pollutant gases in which the pollutant gas-sensitive component of the apparatus can be easily and quickly replaced to permit the apparatus to be used continuously over extended periods of time.

It is another object of the invention to provide apparatus for monitoring pollutant gases in which the detection and measuring of such gases is effected by measuring the change in reflectivity of a pollutant gas-sensitive substrate without the need to employ cumbersome solutions formulated to contain color-forming materials.

It is a related object of the present invention to provide color-forming substrates sensitive to pollutant-containing gases for use with the apparatus of the invention.

These and other objects and advantages of the invention will appear more fully hereinafter, and, for purposes of illustration, but not of limitation, embodiments of the invention are shown in the accompanying drawings in which;

FIG. 1 is a plan view in elevation of apparatus embodying the features of the invention;

FIG. 2 is a schematic illustration of the apparatus of the invention;

FIG. 3 is a perspective view of a gas chamber employed in the apparatus of FIG. 2;

FIG. 4 is a side view in elevation of a cartridge of a pollutant gas-sensitive substrate for use with the apparatus of the invention;

FIG. 5 is a bottom view of the cartridge shown in FIG. 4;

FIG. 6 is a perspective view of a pollutant gas-sensitive substrate prior to exposure, for use with a cartridge of the type shown in FIGS. 4 and 5;

FIG. 7 is a perspective view of the pollutant gas-sensitive substrate of FIG. 6 after exposure to a pollutant-containing gas;

FIG. 10 is a schematic illustration of a control circuit for use with the apparatus of the invention.

Figure 8:
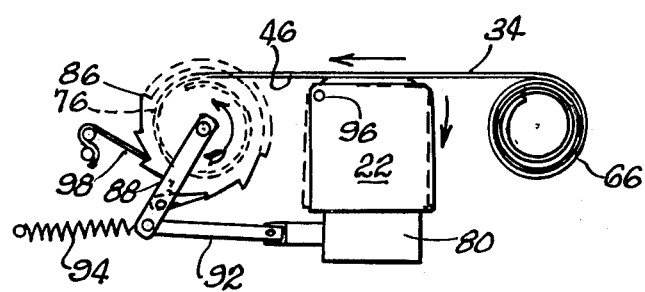
FIG. 8 is a schematic illustration of the drive assembly for advancing the pollutant gas-sensitive substrate in accordance with a preferred form of the invention.

The concepts of the present invention reside in apparatus for monitoring pollutant gases which comprises light source means positioned to pass a beam light angularly onto a light-reflective substrate which is sensitive to one or more pollutant gases and is capable of reaction therewith to produce a loss in reflectivity of the substrate. The light beam incident on the substrate is reflected therefrom, and light-sensing means is positioned to receive the light reflected from the substrate and to measure the decrease in reflectivity of the sensitive substrate as a gas stream containing a pollutant gas is intermittently or continuously contacted with the substrate. The decrease in reflectivity of the substrate and the rate of decrease in reflectivity of the substrate are thus indicative of the concentration of the pollutant gas and the dose rate of pollutant gas to which one is exposed.

In the preferred form of the invention, the apparatus includes a sensing head housing having a pair of oppositely inclined openings communicating each with the other adjacent a central opening, with one of the inclined openings being adapted to receive the light source means and the other of the inclined openings being adapted to receive the light-sensing means. The substrate sensitive to one or more pollutant gases is positioned over the central opening in the housing and, therewith, defines a chamber; the housing is provided with inlet and outlet means to supply a gas stream containing a pollutant gas to the chamber and to permit egress of the gas stream from the chamber.

In the most preferred form of the invention, the pollutant gas-sensitive substrate is in the form of an elongate strip which can be intermittently advanced over the central opening to provide a fresh, reflective surface when the substrate overlaying the central opening has been subjected to sufficient quantities of pollutant gas to result in decreased sensitivity. It has been found that good results are obtained where the substrate is in the form of silica gel coated on to a suitably flexible backing, with the silica gel having been impregnated with components imparting thereto the desired sensitivity to pollutant gases. The substrate can be formed into elongate strips and packaged in the form of removable cartridges including a supply roller and roller for the expended strip in a suitable housing.

The nature of the impregnant used to treat the silica gel depends somewhat on the pollutant gas for which sensitivity is sought. For example, when sensitivity to $NO_2$ is desired the silica impregnated with a mixture of sulfanilic acid and N-(1-naphthyl)-ethylenediamine dihydrochloride which are reactive with $NO_2$ to form color and thereby result in a decrease in the reflectivity of the silica gel coating. For sensitivity to $SO_2$, use can be made of a combination of iodine and 4,4'-methylene-bis-(N,N-dimethylanaline). Lead acetate and palladium chloride can conveniently be used to provide sensitivity to $H_2S$ and carbon monoxide, respectively.

Having described the basic concepts of the invention, reference is now made to the accompanying drawings for a more detailed description of the apparatus of the invention.

There is shown in FIG. 1 an apparatus embodying the features of the invention including a casing 10 having a control panel 12 mounted thereon. As is shown in FIG. 1, the control panel 12 can include an on-off switch 14, means 16 to control the display and alarm means including an alarm 18 and an alarm reset 20 as will be described more fully hereinafter. In addition, the apparatus can, if desired, be provided with display means 21 which is capable of providing the results of the analysis being performed by the apparatus. For this purpose, use can be made of a liquid crystal or light emitting diode display of the type well known to those skilled in the art.

The details as to the operation of the apparatus of the invention is perhaps most clearly shown in FIG. 2 of the drawing which sets forth in schematic form the sensing head and its relation to the sensitive pollutant gas substrate. As shown in this figure, the apparatus includes a sensing head housing 22 which is in the form of a block having a pair of oppositely inclined openings 24 and 26 which converge on a central opening 28 and communicate therewith. One of the inclined openings 24 is adapted to receive the light source means 28 and the other of the inclined openings 26 is adapted to receive the light-sensing means 30.

As will be appreciated by those skilled in the art, the source means can be any of a variety of sources of electromagnetic radiation including an incandescent bulb, a light emitting diode, etc. Similarly, the light-sensing means 30 can be any of a number of devices capable of measuring the intensity of light, including a photo-transistor, a photoelectric cell, a photo-multiplier tube and the like. As can be seen in FIGS. 2 and 3, the central opening 28 is provided with sealing means 32 adapted to provide a sealing relationship between the central opening and the substrate or strip 34 overlaying the central opening 28. Thus, the substrate 34 overlaying the central opening 28 and the sealing means 32 along with the housing 22 define a chamber 36. The housing 22 also includes conduit means 38 to supply a gas stream containing a pollutant gas therein to the chamber 36. As is shown in the drawing, the conduit means 38 includes a tubular portion 40 extending into the housing and a passage 42 communicating with the tubular portion 40 and leading to the chamber 36. As is shown in FIGS. 2 and 3, the conduit means 38 is substantially perpendicular to the plane of a substrate 34, although this has been found not to be necessary, and other configurations may be employed as desired.

The hosing also includes conduit means 44 to provide egress for the gas stream containing the pollutant gas after it has contacted the sensitive substrate 34. As is shown in FIG. 3, the conduit means 44 can simply be a tube extending into the housing and communicating with the chamber 36 to permit the flow of the gas stream containing the pollutant gas therefrom.

As is also shown in FIG. 2, the substrate can be in the form of an elongate strip containing the pollutant gas-sensitive material on the interior face 46 thereof. The elongate strip 34 includes a take-up roll portion 48 and a supply roll portion 50 so that the substrate 34 can be intermittently advanced over the cenral opening 28.

Figure 9:
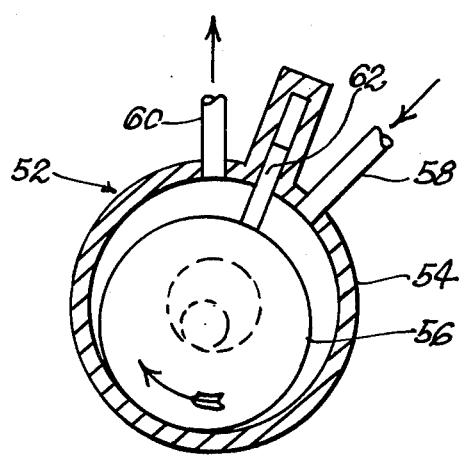
FIG. 9 is a plan view in elevation of a preferred pump for use with the apparatus of the invention.

The gas stream containing the pollutant gas can be supplied to the conduit means 38 for passage to the chamber 36 by means of a pump shown schematically in FIG. 2 as 52. The pump simply draws in the gas sample and displaces it through, if desired, a dryer and/or preconditioner 53 to remove moisture from the gas sample and/or prereact and/or remove interferring substances from the gas sample and into the conduit means 38. It has been found in accordance with the practice of the present invention that low rates of flow of the gas stream are highly desirable because of the high sensitivity of the tape to pollutant gases contained in the gas stream. For this purpose, it has been found that good results are provided with an eccentric pump of the type shown in FIG. 9 of the drawing. As is shown in this figure, the pump includes a housing 54 defining a pump chamber and an eccentric rotor 56 rotatably mounted within the chamber. The housing 54 also includes inlet means 58 and outlet means 60 and a reciprocating seal 62 which is in continuous contact wth the eccentric roller 56 as the roller is rotated within the housing. As will be appreciated by those skilled in the art, as the rotor is rotated in the direction shown by the arrow in the drawing, gas is drawn in through the inlet means 58 into the chamber 54 and is compressed by the eccentric roller 56 and forced out of the chamber 54 through the outlet means 60. Such pumps are of themselves known to those skilled in the art, and have been found highly suitable for use in accordance with the present invention.

The preferred form of the strip or tape 34 forming the substrate which is reflective and sensitive to pollutant gases is shown in FIGS. 4 and 5 of the drawing. As can be seen in these figures, the tape 34 is preferably provided with a cartridge generally designated as 64 including a supply roll housing portion 66 and a take-up roll housing 68 adapted to receive the supply roll 48 and the take-up roll 50 of the tape 34. The housing portions 66 and 68 are joined each to the other by means of a rigid connecting member 70. Each of the housing portions 66 and 68 contains a slot 72 through which the elongate tape can extend whereby the tape 34 is exposed over its length between the housing portions 66 and 68. In this way, the exposed portion of the tape 34 can simply be positioned over the central opening 28 when the cartridge is mounted adjacent to the sensing housing 22.

Each of the housing portions 66 and 68 is provided with suitable rollers 74 and 76 which are adapted to carry the rolls 48 and 50, respectively. Roller 76 as shown in FIG. 4 is provided with means 78 adapted to engage the tape-drive system more fully described hereinafter.

It will thus be apparent to those skilled in the art that the cartridge 64 can simply be inserted into the apparatus of the invention to provide a long-lasting source of the sensitive substrate or strip 34. When the tape 34 has been completely consumed during the analysis or monitoring operation, the cartridge can simply and quickly be removed from the apparatus and be replaced by a fresh cartridge.

The tape 34 itself is shown in FIG. 6 which illustrates the tape prior to exposure to a pollutant gas and FIG. 7, which illustrates the tape after exposure to a pollutant gas. The tape 34 is formed of a flexible backing 80 which is preferably in the form of a flexible plastic material such as Mylar (polyethylene terephthalate) or polyethylene having a coating 82 of silica gel which has been impregnated with the pollutant gas-sensitive material. While silica gel is preferred, it will be apparent that other substrates may also be employed by simply impregnating the substrate with the desired pollutant gas-sensitive materials. For example, reflective paper impregnated with the sensitizing components can be employed as well as a substrate having other porous inert coatings thereon such as alumina coated Mylar, magnesia coated Mylar, etc. As is shown in FIG. 7 of the drawing, the portion of the tape overlaying the central opening 28 is exposed to a pollutant gas and thereby results in a loss of reflectivity of the tape 34. This in effect is indicated by a darkening 84 on the tape in a pattern corresponding to the configuration of the central opening 28. As the tape is exposed to a pollutant gas to provide a loss or decrease in light-reflectivity of the silica gel coating, the tape can simply be advanced by a distance sufficient to provide a fresh portion of the tape 34 overlaying the central opening 28.

The tape-drive mechanism preferred for use with the present invention is shown schematically in FIG. 8 of the drawing. As is shown in this figure, the tape-drive assembly includes a ratchet wheel 86 which is engaged with take-up roll 76 so as to be rotatable therewith. The ratchet wheel 86 is connected to a lever 88 which, when displaced to the right as shown in FIG. 8, causes the ratchet wheel 86 and the corresponding take-up roll 76 to be rotated in the direction shown by the arrow in the drawing. Actuation of the lever 88 is provided by means of a solenoid 90 mounted on the base of the sensing housing 22 and connected to the lever 88 by means of a connecting rod 92. To return the lever 88 to its original position, there is provided spring means 94 which constantly urges the lever 88 toward the position shown in the drawing against the action of the solenoid 90.

In the most preferred form of the invention, the sensing housing 22 is pivotally mounted beneath the strip 34 whereby the sensing housing 22 can be pivoted slightly to release the sealing engagement between the sealing ring 32 about the central opening 28 and the interior surface 46 of the tape. Thus, in operation, as the solenoid is actuated to pull the lever 88 to the right and thereby rotate the ratchet wheel in the direction shown, the solenoid also operates to pivot the sensing housing 22 about the point 96 and thereby disengage the seating relationship between the sealing ring 32 and the surface 46 of the tape 34.

As the ratchet wheel 86 is rotated in the direction shown in the drawing, a locking means 98 is in continuous engagement with the ratchet wheel 86 to thereby prevent displacement of the ratchet wheel 86 in the direction opposite to the direction in which it is advanced by the lever 88. The locking means 98 can simply be in the form of a thin metal strip which is frictionally engaged with the teeth of the ratchet wheel 86. As the ratchet wheel 86 is rotated in the direction shown in the drawing, the locking strip 98 is simply lifted by the teeth on the ratchet wheel 86, without permitting the ratchet wheel to rotate in the opposite direction.

The apparatus of the present invention may also include, as desired, control means to automatically or semi-automatically control the operation of the apparatus. A suitable control system is illustrated schematically in FIG. 10 of the drawing which illustrates the fact that the gas stream containing the pollutant gas therein is passed through the pump 52 through the drying means 53 and into the sensing head 22. The power requirements of the light source means and the light-sensing means can be provided by a power supply 100. The output from the light-sensing means 30 of the sensing head 22 is transmitted to a pulse amplifier circuit 102, and the output of the pulse amplifier circuit 102 is transmitted to the necessary logic circuits 104 which actuate the display 21 and an alarm means 18 as shown in FIG. 10. The details as to the circuitry for the amplifier circuits and the logic circuits form no part of the present invention. However, one sequence which is found to be particularly suitable for operation of the present invention is hereinafter described with reference to FIG. 10 of the drawing.

The logic circuits include timing means whereby, at the beginning of a cycle, the timing means is started, and the light-sensing means 30 measures the intensity of the light reflected from the tape 34. At this point, the pump is started, and the data as to the reflectivity, and specifically the intensity of the light reflected from the tape 34 as determined by the light-sensing means 30 is transferred to the amplifier and hold circuits 102 and accumulated therein. Then, the circuit activates the air pump to cause the air pump to operate for a fixed time interval while the light-sensing means 30 operates to continuously compare the original intensity of the light reflected from the tape with the continuously changing reflectivity of the tape. The alarm can be caused to activate when the rate of decrease in the reflectivity of the tape exceeds a predetermined level, indicating that the dose rate to which an individual is exposed to pollutant gases exceeds a predetermined standard. In addition, the alarm can be programmed to activate when there is a threshold difference between reflectivities, and optionally, when the total exposure as measured by the difference between the original reflectivity from the tape and a subsequent reflectivity from the tape exceeds a predetermined level, such as a level determined to be a maximum dose.

Thereafter, the sequence can be re-started by first moving the tape to advance the tape and thereby provide a fresh unreacted portion of the tape overlaying the central opening 28, and the sequence as described above repeated. It will thus be apparent that the apparatus of the present invention is capable of providing not only a measure of total exposure to a pollutant gas, but also the dose rate of exposure to a pollutant gas in the atmosphere being sampled.

The following examples are provided as illustrative of the practice of the invention in the preparation of pollutant gas-sensitive tapes for use with the apparatus of the invention.

Example I

This example illustrates the preparation of a tape sensitive to $NO_2$.

A coating composition is formulated as follows:

| A coating composition is formulated as follows: | |
|---|---|
| Sulfanilic acid | 1.0% by weight |
| N-(1-naphthyl)-ethylenediamine dihydrochloride | 0.8% by weight |
| Glycerine | 8.0% by weight |
| Water | 90.2% by weight |

The coating composition is then sprayed on a J. T. Baker Co. chromagram sheet which is Mylar coated with silica gel having an average pore size of 100 $\mu$ and including an organic binder for the silica gel. The sheet is then heated to 90° C for about 15 minutes to dry the sheet and to volatilize the organic binder.

EXAMPLE II

The following example illustrates the preparation of a tape sensitive to $SO_2$.

A coating composition is formulated as follows:
| | |
|---|---|
| Solution of iodine and methanol | 1.0% by weight |
| Excess 4,4'-methylenebis-(N,N-dimethylaniline) | 16.0% by weight |
| Glycerine | 5.0% by weight |

The coating composition is then applied to J. T. Baker chromagram sheets in the same manner as described above in reference to Example 1.

EXAMPLE III

The following example illustrates the preparation of a tape sensitive to $H_2S$.

A coating composition is formulated as follows:
| | |
|---|---|
| Lead acetate | 1.0% by weight |
| Glycerine | 20.0% by weight |
| Water | 79.0% by weight |

The foregoing coating composition is then applied to a silica gel coated tape in the same manner as described above in Examples I and II.

It will be understood that various modifications and changes can be made in the details of construction, procedure, formulation and use without departing from the spirit of the invention, especially as defined in the following claims.

I claim:

1. Apparatus for the detection and/or analysis of pollutant gases in a gas stream comprising a light reflective suface sensitive to a pollutant gas for reaction with the pollutant gas to cause a decrease in the reflectivity, light source means positioned to pass a beam of light angularly onto the surface, light-sensing means positioned to receive light reflected from the surface and means to contact a gas stream containing a pollutant gas with the surface whereby the decrease in light reflectivity indicates the concentration of the pollutant gas in the gas stream and the rate of decrease in light reflectivity indicates the dose rate of the pollutant gas in the gas stream.

2. Apparatus as defined in claim 1 which includes a sensing head housing, the housing including a chamber terminating in a central opening adapted to be overlayed by the surface, a pair of oppositely inclined openings, one of said inclined openings adapted to receive the light source means and the other of the inclined openings adapted to receive the light-sensing means, and means to supply the gas streams to the chamber.

3. Apparatus as defined in claim 1 wherein the light source means includes a light emitting diode.

4. Apparatus as defined in claim 1 wherein the light-sensing means includes a photo-transistor.

5. Apparatus as defined in claim 2 wherein the means to supply the gas stream includes pump means.

6. Apparatus as defined in claim 5 wherein the pump means includes a pump having a housing, an eccentric rotor in the housing and a reciprocating sealing member in sealing engagement with the rotor to provide a low flow rate of the gas stream.

7. Apparatus as defined in claim 2 wherein the reflective surface is in the form of an elongate strip adapted to be advanced over the central opening.

8. Apparatus as defined in claim 7 which includes a cartridge housing for the strip, said housing including a supply roller housing portion, a take-up roll housing portion, a connecting member between the housing portions, said connecting member including an opening about the central opening, and means to advance the strip over the central opening.

9. Apparatus as defined in claim 8 wherein the sensing head housing is pivotally mounted adjacent to the cartridge housing, with the sensing head housing being pivoted away from the tape in response to actuation of the means to advance the strip.

10. Apparatus as defined in claim 8 wherein the means to advance the strip includes a toothed wheel fixed to one end of the strip whereby rotation of the toothed wheel advances the strip, a solenoid, and lever fixed to the toothed wheel, with the lever being actuated by the solenoid whereby activation of the lever by the solenoid causes rotation of the toothed wheel.

11. Apparatus as defined in claim 1 wherein the tape is formed of a backing having a coating thereon, said coating comprising silica impregnated with a pollutant gas-sensitive material.

12. Apparatus for the detection and/or analysis of pollutant gases in a gas stream comprising a sensing head housing, said housing including a chamber terminating in a central window, a pair of oppositely inclined openings adjacent to said window, a light reflective surface sensitive to a pollutant gas capable of reaction with the pollutant gas to cause a decrease in the reflectivity of said surface, with the surface positioned overlaying said window, light source means positioned in one of the pair of openings to pass a beam of light angularly onto said surface, light sensing means positioned in the other of the pair of openings to receive light reflected from the surface, and means to supply the gas stream containing the pollutant gas to said chamber for reaction with said surface to cause a decrease in the reflectivity whereby the decrease in the light reflectivity of said surface is determined by the light sensing means as a measure of the concentration of the pollutant gas in the gas stream and the rate of decrease in light reflectivity is determined as a measure of the dose rate of the pollutant gas in the gas stream.

13. Apparatus for the detection and/or analysis of pollutant gases in a gas stream comprising
   1. a sensing head housing, said housing including a chamber terminating in a central opening and a pair of oppositely inclined openings in the housing communicating with the chamber,
   2. a light reflective surface carried by an elongate tape adapted to overlay the central opening and be advanced thereover, said surface being sensitive to the pollutant gases to react therewith and cause a decrease in the light reflectivity of the surface,
   3. light source means mounted in one of the inclined openings and positioned to pass a beam of light onto said surface,
   4. light sensing means mounted in the other of the inclined openings and positioned to receive light reflected from the surface,
   5. means to supply a gas stream containing a pollutant gas to said chamber for reaction with the surface to cause a decrease in the reflectivity thereof whereby the decrease in the light reflectivity of the surface is measured by the light sensing means to determine the concentration of the pollutant gas in the gas stream and the rate of decrease in light reflectivity is measured to determine the dose rate of the pollutant gas in the gas stream, and
   6. means to advance the tape across the central opening.

* * * * *